United States Patent
Eury, Jr.

(10) Patent No.: US 9,907,924 B2
(45) Date of Patent: Mar. 6, 2018

(54) SEALING CUSHION HAVING CORRUGATED SEALING FLAP

(71) Applicant: KONINKLIJKE PHILIPS N.V., Eindhoven (NL)

(72) Inventor: Matthew Paul Eury, Jr., Latrobe, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 250 days.

(21) Appl. No.: 14/406,555

(22) PCT Filed: May 28, 2013

(86) PCT No.: PCT/IB2013/054392
§ 371 (c)(1),
(2) Date: Dec. 9, 2014

(87) PCT Pub. No.: WO2013/186650
PCT Pub. Date: Dec. 19, 2013

(65) Prior Publication Data
US 2015/0157823 A1 Jun. 11, 2015

Related U.S. Application Data

(60) Provisional application No. 61/658,471, filed on Jun. 12, 2012.

(51) Int. Cl.
*A61M 16/06* (2006.01)
*A61M 16/00* (2006.01)

(52) U.S. Cl.
CPC .... *A61M 16/0622* (2014.02); *A61M 16/0057* (2013.01); *A61M 16/06* (2013.01);
(Continued)

(58) Field of Classification Search
CPC ....... A61M 16/06–16/0655; A61M 2016/0661
See application file for complete search history.

(56) References Cited

U.S. PATENT DOCUMENTS 4,770,169 A * 9/1988 Schmoegner ......... A61M 16/08
128/206.24
4,907,584 A 3/1990 McGinnis
(Continued)

FOREIGN PATENT DOCUMENTS

CN 1784250 A 6/2006
CN 102014999 A 4/2011
(Continued)

*Primary Examiner* — Rachel T Sippel
(74) *Attorney, Agent, or Firm* — Michael W. Haas

(57) ABSTRACT

A cushion (26) for a patient interface device includes a support wall portion having a first edge and an opposite second edge, and a sealing flap (40) extending in a cantilevered fashion inwardly from the second edge and toward a longitudinal axis of the cushion such that when the patient interface device is donned a portion of the face of the user will engage the top outer surface of the sealing flap to form a seal. The sealing flap includes a corrugated portion (56), wherein the corrugated portion commences at a distal edge of the sealing flap and extends toward a proximal edge of the sealing flap along at least a portion of a width of the sealing flap. The corrugated portion includes a series of alternating furrows and ridges.

18 Claims, 16 Drawing Sheets

(52) U.S. Cl.
CPC .... *A61M 16/0611* (2014.02); *A61M 16/0616* (2014.02); *A61M 16/0633* (2014.02); *A61M 16/0683* (2013.01)

(56) References Cited

U.S. PATENT DOCUMENTS

| | | |
|---|---|---|
| 2006/0130844 A1 | 6/2006 | Ho |
| 2007/0125384 A1* | 6/2007 | Zollinger .............. A61M 16/06 128/206.24 |
| 2008/0006277 A1 | 1/2008 | Worboys |
| 2008/0223373 A1 | 9/2008 | Chang |
| 2011/0186051 A1* | 8/2011 | McAuley .............. A61M 16/06 128/206.24 |
| 2012/0289851 A1* | 11/2012 | Varga .................. A61B 5/0836 600/532 |

FOREIGN PATENT DOCUMENTS

| | | |
|---|---|---|
| JP | 2008264026 A | 11/2008 |
| WO | WO2006074514 A1 | 7/2006 |
| WO | WO2007021777 A2 | 2/2007 |
| WO | WO2009108995 A1 | 9/2009 |
| WO | WO2010016774 A1 | 2/2010 |
| WO | WO2010148453 A1 | 12/2010 |
| WO | WO2011060479 A1 | 5/2011 |
| WO | WO2011121463 A1 | 10/2011 |

* cited by examiner

SEALING CUSHION HAVING CORRUGATED SEALING FLAP

CROSS-REFERENCE TO RELATED APPLICATIONS

This patent application claims the priority benefit under 35 U.S.C. § 371 of international patent application no. PCT/IB2013/054582, filed Jun. 4, 2013, which claims the priority benefit under 35 U.S.C. § 119(e) of U.S. Provisional Application No. 61/658,471 filed on Jun. 12, 2012, the contents of which are herein incorporated by reference.

BACKGROUND OF THE INVENTION

1. Field of the Invention

The present invention pertains to patient interface devices structured to deliver a flow of breathing gas to a user, and, in particular, to a sealing cushion for a patient interface device that has a corrugated sealing flap.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The sealing cushion typically has a support portion coupled to a sealing flap portion, which may integrated together as a single part or that may be separate components that when combined together in the final assembly provide the sealing and support functions. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Patient interface devices used in non-invasive ventilation and pressure support therapies should be comfortable and maintain a robust seal, while at the same time optimizing comfort by avoiding the creation of excessive pressure and/or red marks on the user's face. The sealing flap portion should also conform to the face without excessive bunching and encroaching on the patient's eyes, cheeks, and nostrils. As used herein, the term "bunching" shall refer to an area where, when the sealing cushion is donned by the user, extra sealing flap length collects and folds/curls over itself, resulting in bunches or folds of sealing flap. Bunching can cause patient annoyance, obstruct the patient's view, partially obstruct the patient's air path, and/or create potential leak paths, any or all of which may ultimately decrease the patient's therapy compliance.

Unfortunately, many current patient interface devices used in non-invasive ventilation and pressure support therapies have sealing problems, create pressure on the face, and/or cause red marks and/or sores. One location where such problems, especially pressure points, frequently occur is on and around the bridge of the nose where the sealing flap seals against the patient.

These problems are primarily due to the geometry utilized in current sealing cushions. In particular, traditionally, patient interface devices have sealing flaps which either (i) are all convex without any reversals along the opening circumference (i.e., distal end) of the sealing flap, or (ii) have a single change in the flap opening geometry from convex to concave. This creates a finite arc length of the sealing flap distal end defining the sealing flap opening that must conform to an infinite number of potential patient facial (e.g., nose bridge) geometries. The traditional designs of one or no reversals in the sealing flap opening circumference must therefore rely on the flexibility and elongation of the material used to stretch and conform to all patient faces. However, because the length of the sealing flap distal end is finite, when compressed against the patient's face, it tends to create excess pressure and resultant red marks across and on the patient's face (e.g., at the bridge of the patient's nose). This is due to the sealing flap compressing against the face and applying compressive, tensile, and shear forces all at the same time and in multiple directions. For example, using the nose bridge as one particular illustration, as the sealing cushion is compressed and tightened against the face, the finite opening circumference of the sealing flap (typically made of an elastomeric material such as TPE, silicone, rubber, etc.) must flex and stretch into the nose bridge (−z direction), up or down the nose bridge (+y or −y direction) and across the nose bridge (+ and −x directions) as it conforms to the patient's nose to create a seal.

In traditional designs, attempts are often made to make a sealing cushion having a sealing flap that will fit all patient nose bridges and depths. However, if the length of the flap is not a perfect match for a particular user, negative fit and comfort situations will likely occur. Specifically, on some patients, the sealing flap will be too short and will not fully seat against the nose. As a result, a robust seal may not be formed and/or the sealing flap will stretch too tightly across the nose bridge and cause excessive pressure and red marks. On other patients, the same sealing flap will be too long and will bunch at the patient's eyes and encroach on their vision and/or create leak paths (because the flap's excess length mistakenly and easily locates the top arc of the sealing flap too high on the nose towards the eyes). Alternatively, because of the flap's excess length, it is more likely to mistakenly and easily locate the top arc of the sealing flap too high on the nose towards the eyes, when donned by the user. At such an incorrect location (+ or −y direction), the sealing flap will often too tightly stretch across the nose bridge and therefore causes excessive pressure and red marks.

To remedy these issues, traditional designs have either increased the sealing flap height and depth or decreased the sealing flap height and depth. The problem with these approaches is that each creates additional problems for patients with the opposing facial geometry.

Thus, in short, for traditional sealing flaps, if the circumference of the flap opening is too short and is located at an insufficient height from the interface, it will need to stretch and flex more than desired, or even possible because of material properties, in the x, y, and z directions, especially at the nose bridge areas, in order to create a seal. This will cause excess force and shear against and in line with the nose and skin, which causes discomfort, pressure, and/or red marks. This may also cause leak issues on facial geometries with deep nose features because the flap is too short to form a robust sealing surface area against the face. If the circumference of the flap opening is too long and is located at an excessive height from the interface, there may be seal issues and bunching of the sealing flap. This may cause patient annoyance and discomfort as well as creating potential leak paths. The only way in the current art to alleviate the problem of pressure and red marks on the nose bridge (or other facial areas) is to have multiple sizes (sizes being different circumference openings and sealing flap heights) of each design available to accommodate different facial geometries.

SUMMARY OF THE INVENTION

Accordingly, it is an object of the present invention to provide a cushion for a patient interface device that overcomes the shortcomings of conventional cushions. This object is achieved according to the present invention by providing cushion that includes a corrugated sealing flap.

In one embodiment, a cushion for a patient interface device is provided that includes a support wall portion having a first edge and a second edge located opposite the first edge, and a sealing flap extending in a cantilevered fashion inwardly from the second edge and toward a longitudinal axis of the cushion such that when the patient interface device is donned by a user a portion of the face of the user will engage a top outer surface of the sealing flap to form a seal therewith. The sealing flap includes a corrugated portion, wherein the corrugated portion commences at a distal edge of the sealing flap which defines an opening in the sealing flap and extends toward a proximal edge of the sealing flap along at least a portion of a width of the sealing flap including the top outer surface. The corrugated portion includes a series of alternating furrows and ridges, wherein the number of the furrows is at least two or the number of the ridges is at least two.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
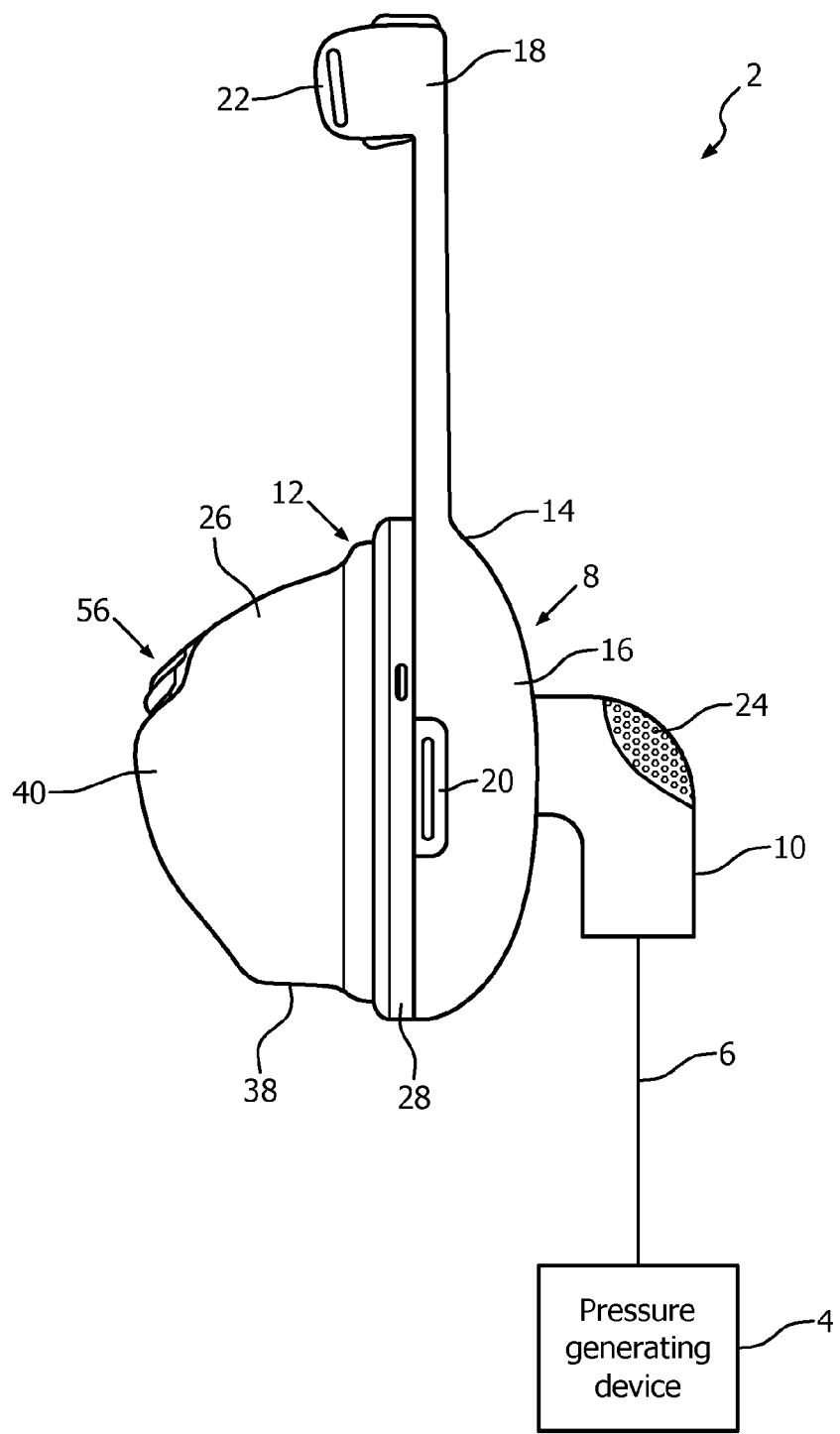
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As described in detail herein, the invention provides a sealing cushion that utilizes corrugations or waves in the opening circumference of the sealing flap in order to reduce pressure points (e.g., at the nose bridge or other locations) and/or red marks without the need of multiple designs (a single design would conform to multiple patient facial geometry). As detailed herein, the sealing flap is structured to flex, stretch and conform to the face without creating additional compressive and shear force to the areas where the corrugations or waves are implemented.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8 including an elbow conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and autotitration pressure support devices. Delivery conduit 6 is structured to communicate the flow of breathing gas from pressure generating device 4 to patient interface device 8.

In the illustrated embodiment, patient interface device 8 comprises a nasal mask structured to cover the nose of the patient. However, other types of patient interface devices 8, such as, without limitation, a nasal/oral mask that covers the patient's nose and mouth, or a full face mask that covers the patient's face, which facilitates the delivery of the flow of breathing gas to, and the removal of a flow of exhalation gas from, the airway of a patient may be used while remaining within the scope of the present invention. In the embodiment shown in FIG. 1, patient interface device 8 includes a cushion assembly 12 and a frame member 14 having a faceplate portion 16 and a forehead support portion 18. Frame member 14 is made of a rigid or semi-rigid material, such as, without limitation, an injection molded thermoplastic or silicone. Straps (not shown) of a headgear component may be attached to faceplate portion 16 via attachment members 20 and to forehead support portion 18 via attachment members 22 to secure patient interface device 8 to the patient's head. An opening in faceplate portion 16 to which elbow conduit 10 is coupled allows the flow of breathing gas from pressure generating device 4 to be communicated to an interior space defined by faceplate portion 16 and cushion assembly 12, and then, to the airway of a patient. The opening in faceplate portion 16 also allows the flow of exhalation gas (from the airway of such a patient) to be communicated to exhaust vent 24 provided in elbow conduit 10.

Figure 2:
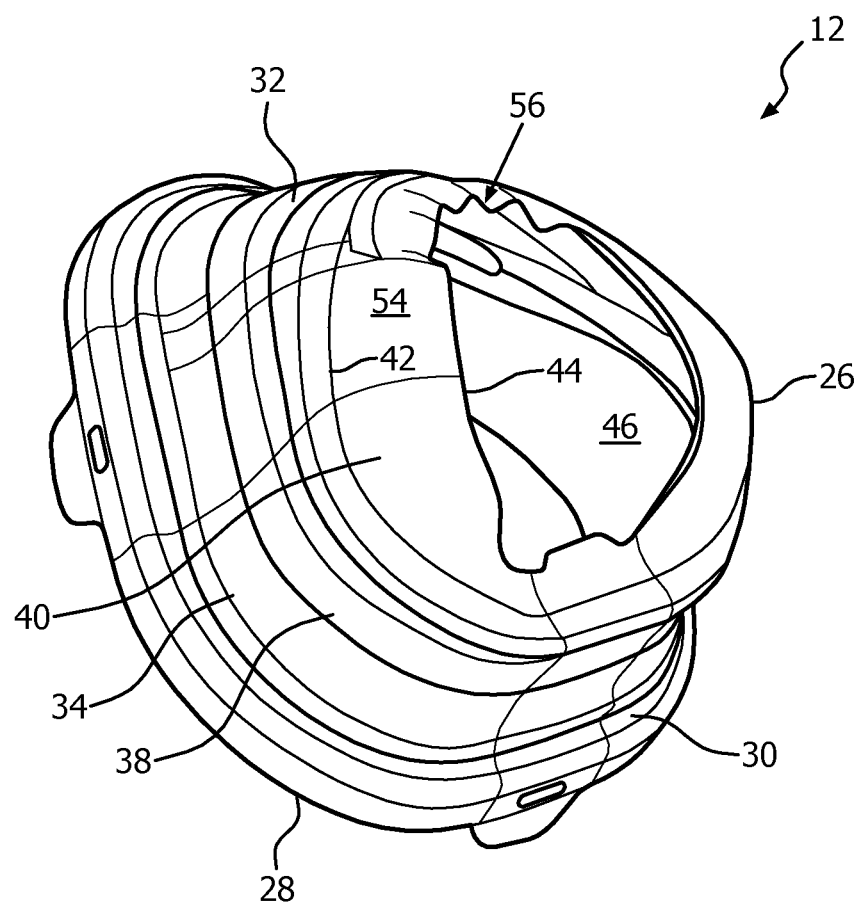
FIG. 2 is a side isometric view.
Figure 3:
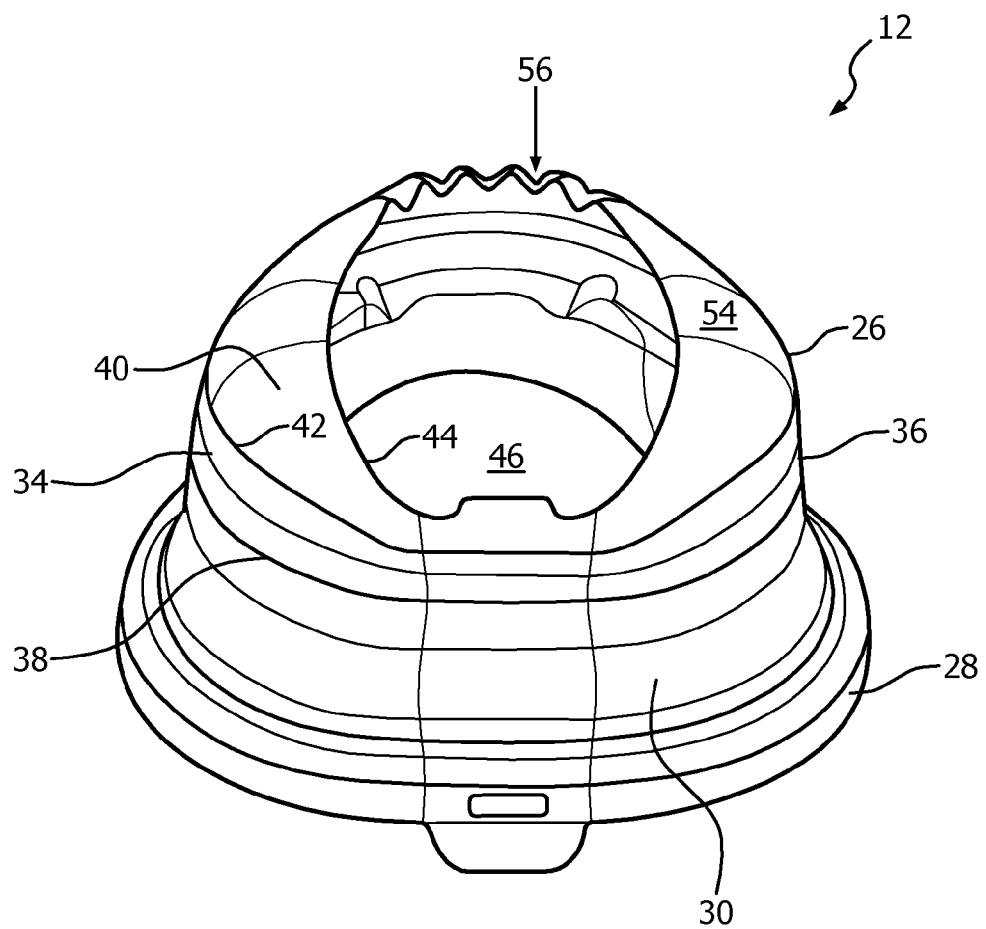
FIG. 3 is a front isometric view.
Figure 4:
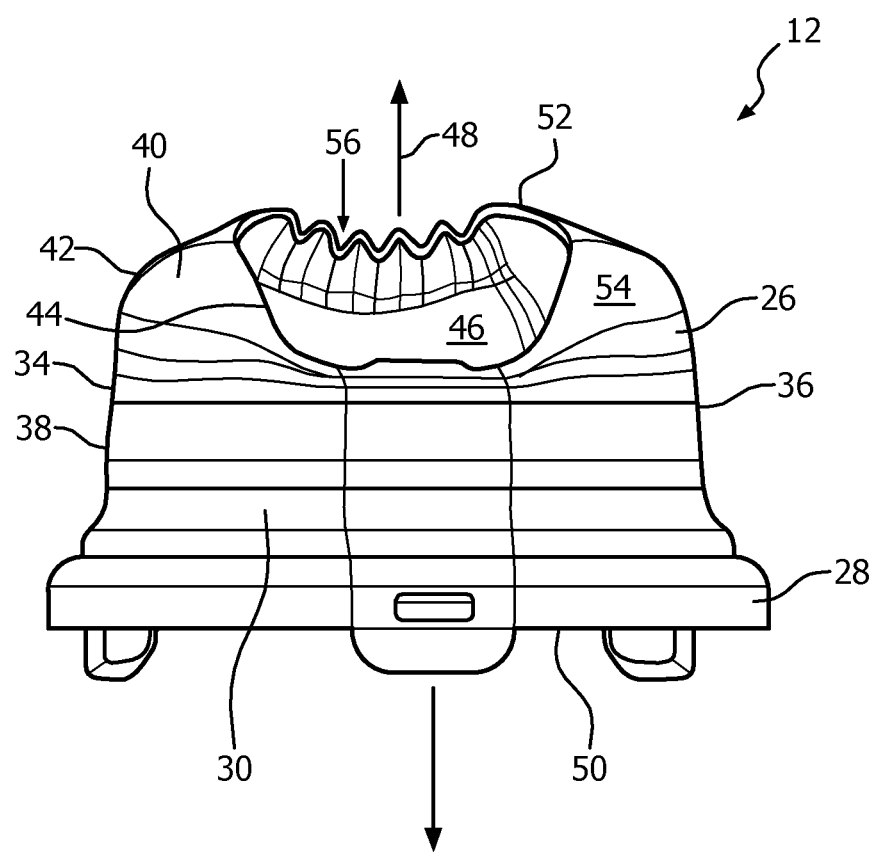
FIG. 4 is a front elevational view.
Figure 5:
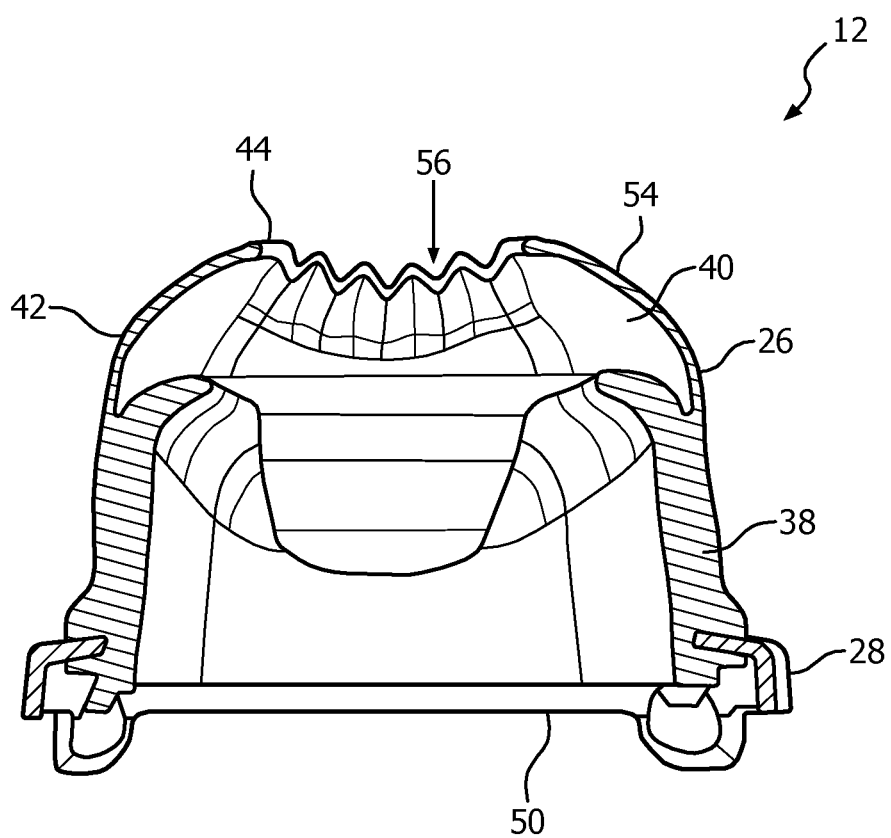
FIGS. 5 and 6 are cross-sectional views of a cushion assembly forming a part of a patient interface device of the system of FIG. 1.
Figure 6:
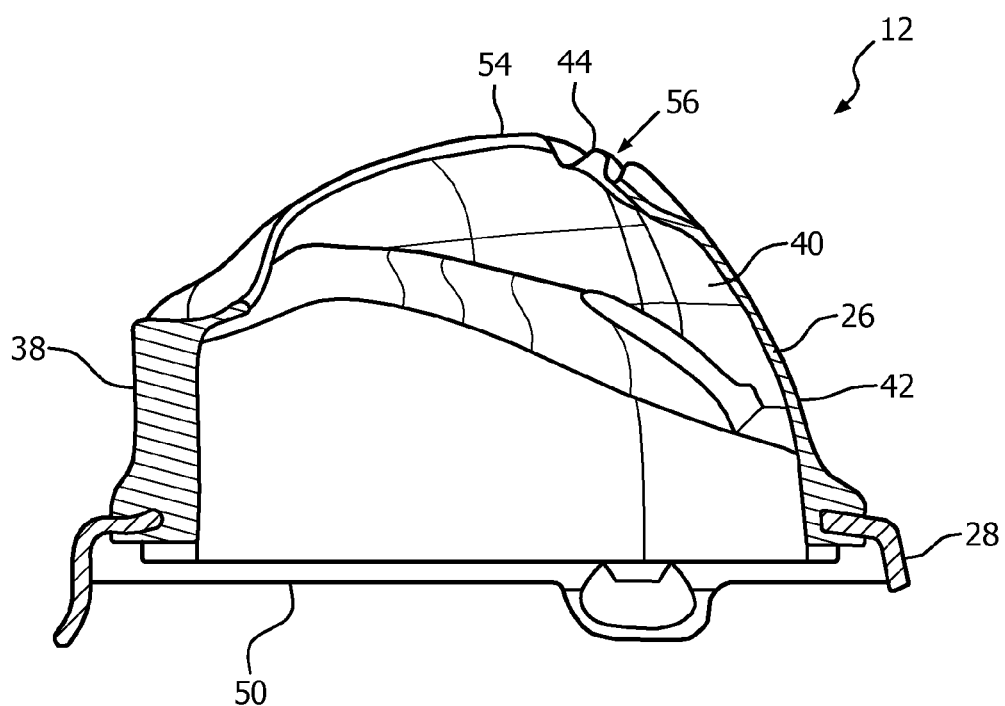

FIG. 2 is a side isometric view, FIG. 3 is a front isometric view, FIG. 4 is a front elevational view, and FIGS. 5 and 6 are cross-sectional views of cushion assembly 12 according to one non-limiting exemplary embodiment of the present in invention. Cushion assembly 12 includes a cushion member 26 coupled to a support ring 28. Support ring 28 is made from a rigid or semi-rigid material, such as, without limitation, an injection molded thermoplastic or silicone, and facilitates secure fluid connection of cushion assembly 12 to frame member 14.

In the exemplary embodiment, cushion member 26 is defined from a unitary piece of soft, flexible, cushiony, elastomeric material, such as, without limitation, silicone or an appropriately soft thermoplastic elastomer, or any combination of such materials. It will be understood, however, that cushion member 26 does not need to be unitary within the scope of the present invention. Rather, cushion member 26, and the parts thereof, may be made of separate components (e.g., separate sealing flap and support portion) that are coupled to one another by suitable means. Also in the exemplary embodiment, cushion assembly 12 has a generally triangular shape including a bottom region 30, an apex region 32 located opposite bottom region 30, a first side region 34 and a second side region 36 located opposite first side region 34. As a result, both cushion member 26 and support ring 28 will have associated bottom, apex and first and second side regions.

Cushion member 26 includes an outer wall 38 comprising a support portion of cushion member 26 and a sealing flap 40 that extends inwardly from outer wall 38. As seen in FIGS. 2-4, sealing flap 40 includes a proximal end 42 coupled to the top edge of outer wall 38 and a distal end 44 opposite proximal end 42, wherein distal end 44 defines an opening 46 structured to receive the patient's nose. Sealing flap 40 thus extends in a direction that is transverse to a longitudinal axis 48 (FIG. 4) of cushion assembly 12, wherein longitudinal axis 48 extends from the rear 50 of cushion assembly 12 where cushion assembly 12 attaches to frame member 14 to the front 52 of cushion assembly 12 (longitudinal axis 48 thus defines the general direction in which gasses flow through cushion assembly 12).

In addition, in the exemplary embodiment, outer wall 38 extends outwardly from support ring 28 in a direction that is generally parallel to longitudinal axis 48 and generally perpendicular to the plane defining rear 50 of cushion assembly 12. Sealing flap 40 thus extends in an angled (e.g. upwardly or downwardly with respect to the plane just described; in the illustrated embodiment, it extend upwardly), cantilevered fashion from the top edge of outer wall 38 such that when patient interface device 8 is donned by the user, the user's face (e.g., nose bridge, cheeks and area above the upper lip) will directly engage the top, outer surface 54 of sealing flap 40 to form a seal therewith. In one exemplary embodiment, the angle of sealing flap 40 may be upwardly/outwardly 85° from the plane defining rear 50 of cushion assembly 12, to downwardly/inwardly −85° from the plane defining rear 50 of cushion assembly 12.

Figure 7:
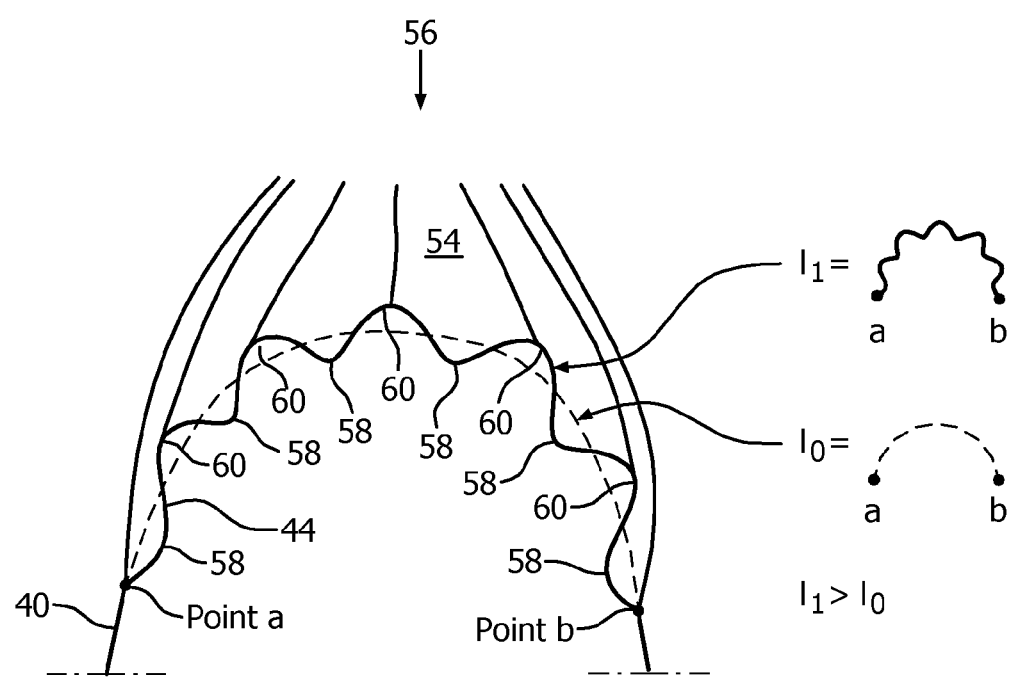
FIG. 7 is a schematic illustration of a corrugated portion of the cushion assembly of FIGS. 2-6 according to one embodiment.

In addition, sealing flap 40 of cushion member 26 includes a corrugated portion 56, which is shown schematically in FIG. 7. In the illustrated, non-limiting exemplary embodiment, corrugated portion 56 is provided at the apex region of cushion member 26 such that it will be directly engaged by the nose bridge of the user. As used herein, and referring to FIG. 7, the term "corrugated portion" shall refer to a portion of sealing flap 40 that commences at distal edge 44 of sealing flap 40 (which defines the perimeter opening 46) and that extends either partially or fully toward/to proximal edge 42 along the width of sealing flap 40 and that includes a series of alternating furrows 58 (also referred to as valleys) and ridges 60 (also referred to as peaks), wherein the corrugated portion 56 includes at least two furrows 58 and at least one ridge 60, or at least one furrow 58 and at least two ridges 60.

In particular embodiments, as described herein, corrugated portion 56 includes at least two furrows 58 and at least two ridges 60. As seen in FIG. 7, corrugated portion 56 will have a lateral length $l_1$ measured at distal edge 44 and from point a (the beginning lateral side of corrugated portion 56) to point b (the ending lateral side of corrugated portion 56) that is longer than a lateral length $l_0$ of a prior art non-corrugated portion (represented by the dashed lines in FIG. 7) of a sealing flap that would extend between the same two points (a and b). Thus, corrugated portion 56 will increase the actual opening circumference of sealing flap 40 (it will create a longer arc length because $l_1 > l_0$) without increasing its opening area or height/depth as compared to the prior art non-corrugated portion shown in FIG. 7.

In addition, the overall shape of corrugated portion 56 will be determined by the amplitude of each furrow 58 and each ridge 60 (which may be uniform or vary within corrugated portion 56), the wavelength measured from the beginning of a ridges 60 to an immediately adjacent furrow 58) (which may be uniform or vary within corrugated portion 56), the radius of curvature of each furrow 58 and each ridge 60 (which may be uniform or vary within corrugated portion 56), and the length of each furrow 58 and each ridge 60 (i.e., the distance each extends from distal edge 44 toward proximal edge 42) (which may be uniform or vary within corrugated portion 56). Thus, corrugated portion 56 may be used to increase the opening circumference of sealing flap 40 by any desired percentage, and the increase in circumference may be controlled by the amplitude, wavelength, and/or radii of the furrows 58 and ridges 60 that comprise the corrugated portion 56. Furthermore, the length of each furrow 58 and each ridge 60 will control the possibility of leak paths, and in one embodiment, such lengths are made short enough to create a robust seal at and past the point on sealing flap 40 where furrows 58 and ridges 60 end. This all occurs without increasing or decreasing the flap height and without increasing or decreasing the area of the sealing flap opening, and will reduce pressure and red marks.

In one particular, non-limiting exemplary embodiment corrugated portions 56 may utilize a soft material having a durometer of 35 to 55 Shore 00, with a material thickness of 0.05 mm to 1 mm, with a furrow to ridge (immediately adjacent to one another) total amplitude range of 2 mm to 3 mm within the corrugated portions 56, and with a wavelength (measured using immediately adjacent furrows and ridges) range of 4 mm to 5 mm within the corrugated portions 56. As will be appreciated, this will result in a total amplitude to wavelength ratio (using immediately adjacent furrows and ridges) within corrugated portion 56 of 0.4 to 0.75. In one specific implementation, that ratio is 0.5 (1:2) throughout corrugated portion 56. In addition, this embodiment may employ a ridge and furrow radii (radius of curvature) of 1 mm to 2 mm, with a furrow/ridge length of 11 mm to 13 mm. It will be understood, however, that in other embodiments other combinations of durometer, thickness, furrow/ridge length, amplitude, wavelength, and radii may be utilized. As material properties change, the relationship and ratios between the aforementioned specifications would be modified to achieve the same effect of increasing the circumference of the sealing flap opening by the corrugations elongating and flattening. As the materials used get softer, the thickness and amplitude of corrugated portions 56 may increase while decreasing wavelength and radii to achieve the desired effect.

As the materials used get harder, the thickness and amplitude may be decreased and the wavelength and radii may be increased for the desired effect. Combinations of these or other increasing and decreasing ratios may be utilized to optimize the desired effect of increasing the circumference of the sealing flap opening by the corrugations elongating and flattening. The properties of the materials chosen (most importantly durometer and elongation) will drive the ratio and relationship between the aforementioned geometry for optimization of increasing the circumference of the sealing flap opening by the corrugations elongating and flattening. A wider range of these properties and geometries may be: durometer 00 to 90 Shore 00, 0.2 mm to 2 mm for sealing flap thickness, ridge to furrow amplitude 1 mm to 10 mm, wavelength 1 mm to 8 mm, radii 0.05 mm to 5 mm, ridge/furrow length 1 mm to 30 mm. The ratio of total amplitude to wavelength would ideally be 1:2, but may vary to optimize the effect of increasing the circumference of the sealing flap opening by the corrugations elongating and flattening. It should be noted that these are not specifications or limitations to the invention geometry and that any combination or ratio thereof may be utilized for the invention. These would need to be optimized to optimize the effect of increasing the circumference of the sealing flap opening by the corrugations elongating and flattening.

Corrugated portion 56 is thus advantageous as it will allow cushion member 26 to automatically adjust to different facial depths and geometries. More specifically, corrugated portion 56 will readily conform to multiple facial geometries and depths in response to top outer surface 54 being engaged since corrugated portion 56 provides, at a focused location, additional flap length without increasing the height/depth of sealing flap 58 and without creating bunching. Furrows 58 and ridges 60 will conform against the user's face when it engages the top, outer surface 54 of sealing flap 40, and will provide the additional stretch and flex needed for those with deeper features (e.g., deeper noses), yet will still seal against the face of those with shallower features (e.g., noses). Corrugated portion 56 thus eliminates the need for different designs and/or heights/depths to fit different nose depths and facial geometries.

Corrugated portion 56 also reduces the chances that sealing flap 40 will be too short on certain user faces and reduces the possibility of excess pressure and red marks because the sealing flap height does not need to be reduced for patients with shallower noses or other facial geometries.

Moreover, in the illustrated exemplary embodiment wherein corrugated portion 56 is provided at the apex region of cushion member 26, corrugated portion 56 will minimize the compressive force (−z direction) at the nose bridge because of the depth of furrows 58 and ridges 60 at that localized area. As stated above, furrows 58 and ridges 60 will provide an arc length at the apex region of sealing flap 40 defining opening 46 that is longer and much more flexible and stretchable than a flap without corrugated portion 56. As strapping force is applied to the patient interface device 8, furrows 58 and ridges 60 will flatten out, thereby increasing the arc length and absorbing the force. Furrows 58 and ridges 60, and the additional arc length and flex they provide, will also reduce the shear (+ and −x and y directions) across and up and down the nose bridge.

Corrugated portion 56 thus provides a dynamic sealing cushion solution. More particularly, as patient interface device 8 is tightened against the user's face, the amplitude of furrows 58 and ridges 60 will decrease, the wavelength of furrows 58 and/or ridges 60 will increase, the radii of furrows 58 and ridges 60 will increase, and the material of sealing flap 40 will stretch, with the end result being a continuous arc. The pressure and shear, however, are reduced, thereby reducing the potential for red marks as compared to traditional designs. Corrugated portion 56 absorbs the force and shear instead of the skin on the nose bridge. This is in contrast to a traditional, non-corrugated sealing flap which presses tighter against the nose and creates shear on the skin immediately upon contact between the flap and the face. Such a non-corrugated flap will immediately, upon contact and having −z direction force applied, begin to compress and shear against the skin because elongation and stretch of the sealing flap material is the sole feature to absorb force. In the present invention, it takes less force and causes less shear to flatten furrows 58 and ridges 60 until they are flush with the skin.

Figure 8:
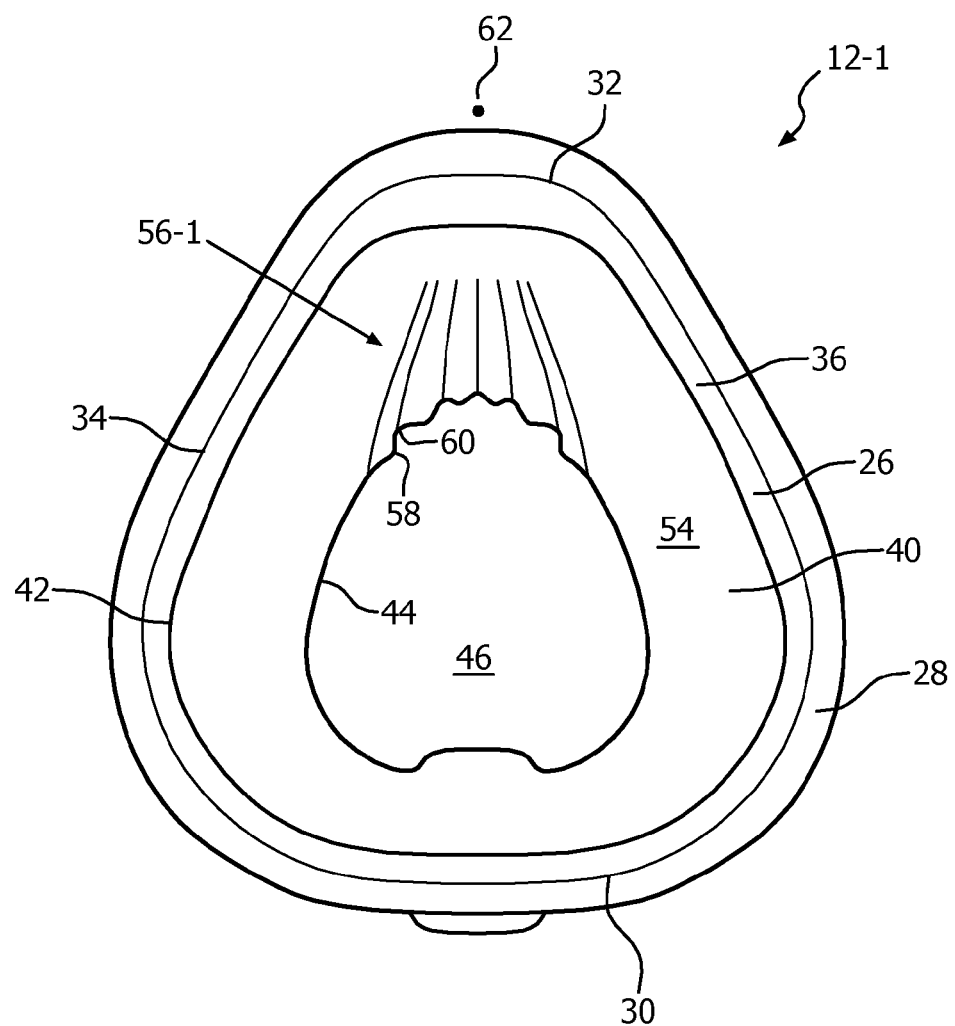
FIGS. 8-13 are schematic illustrations of cushion assemblies according to various alternative exemplary embodiments that may form a part of the patient interface device of the system of FIG. 1.
Figure 9:
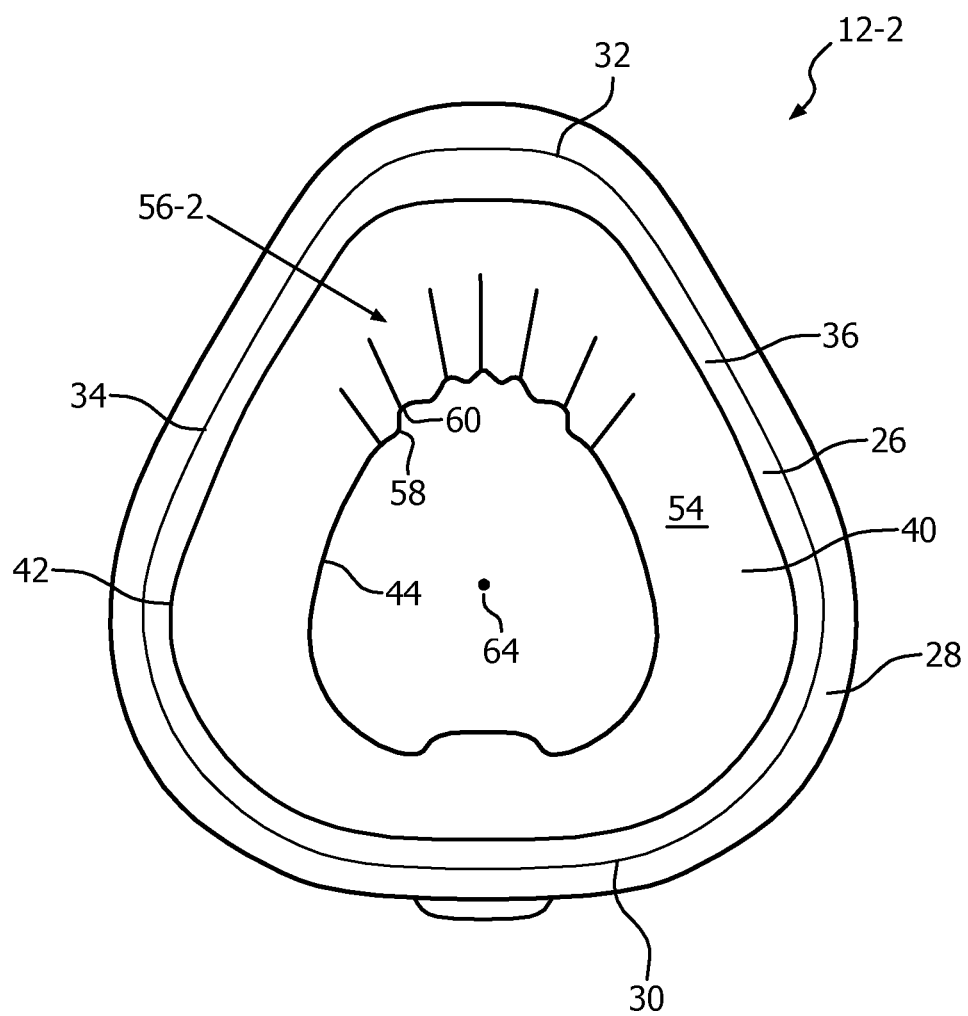

FIG. 8 is a schematic illustration of a cushion assembly 12-1 according to an alternative particular, non-limiting exemplary embodiment. In cushion assembly 12-1, corrugated portion 56-1 is constructed such that furrows 58 and ridges 60 are formed in an array on an arc wherein all of the furrows 58 and all of the ridges 60 have a common focal point 62 that is above the apex region of opening 46. FIG. 9 is a schematic illustration of a cushion assembly 12-2 according to another alternative particular, non-limiting exemplary embodiment. In cushion assembly 12-2, corrugated portion 56-2 is constructed such that furrows 58 and ridges 60 are formed in an array on an arc wherein all of the furrows 58 and all of the ridges 60 have a common focal point 64 that is below the apex region of opening 46. It will be understood, however, that corrugated portions 56-1 and 56-2 are exemplary only, and that furrows 58 and ridges 60 do not need to be formed in an array with a common focal point. Rather, in alternative embodiments, furrows 58 and ridges 60 may be straight, horizontal, vertical, or on an angle.

Figure 10:
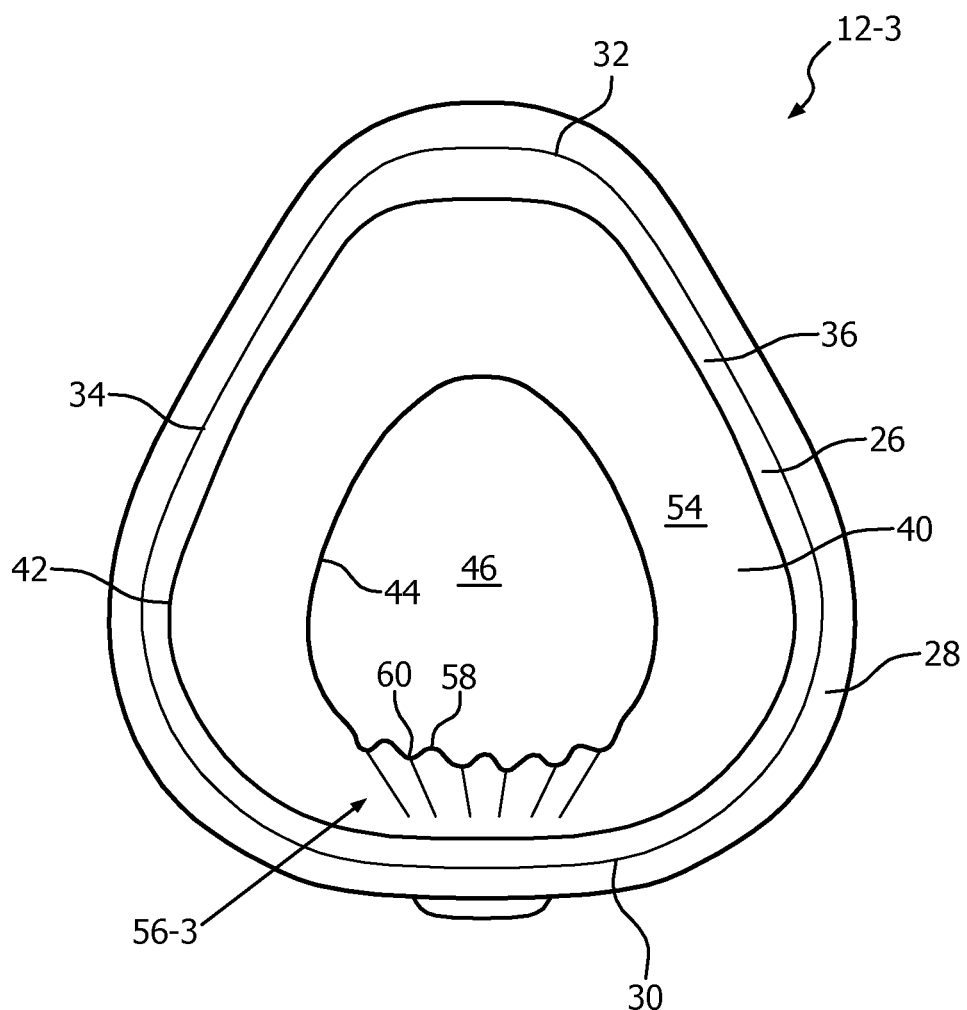

Furthermore, while in the embodiments shown in FIGS. 1-9, corrugated portion 56 is provided in the apex region of sealing flap 40 such that it will be engaged by the bridge of the user's nose, it will be understood that that is but one example implementation of the present invention and that a corrugated portion 56 may be provided in one or more other portions of sealing flap 40 (anywhere around sealing flap 40). For example, FIG. 10 is a schematic illustration of a cushion assembly 12-3 according to another particular, non-limiting exemplary embodiment wherein corrugated portion 56-3 is provided in the bottom region of sealing flap 40 such that it will be engaged by the portion of the patient mouth above the upper lip. In addition, in the non-limiting illustrated embodiment of cushion assembly 12-3, corrugated portion 56-3 is constructed such that furrows 58 and ridges 60 are formed in an array on an arc wherein all of the furrows 58 and all of the ridges 60 have a common focal point (below the bottom region of opening 46 in the illustrated embodiment, although it may also be above the bottom region of opening 46).

Figure 11:
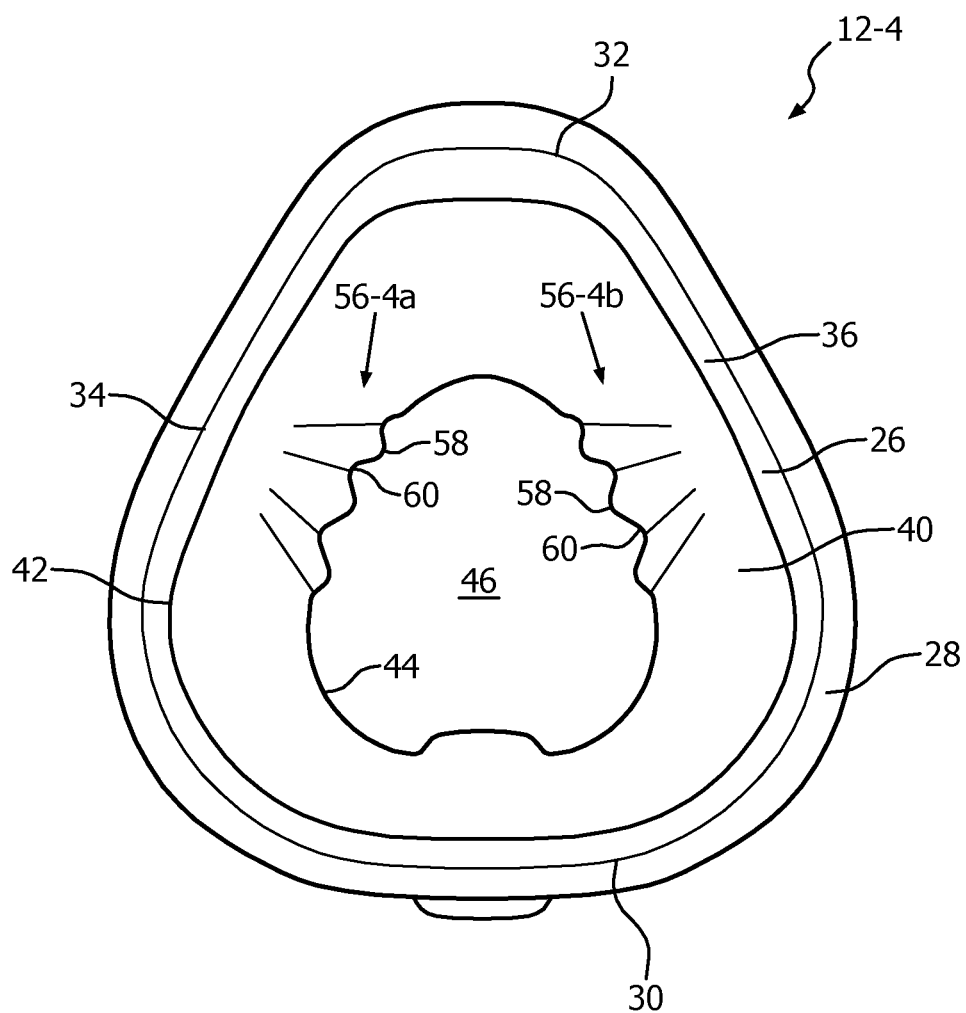
Figure 12:
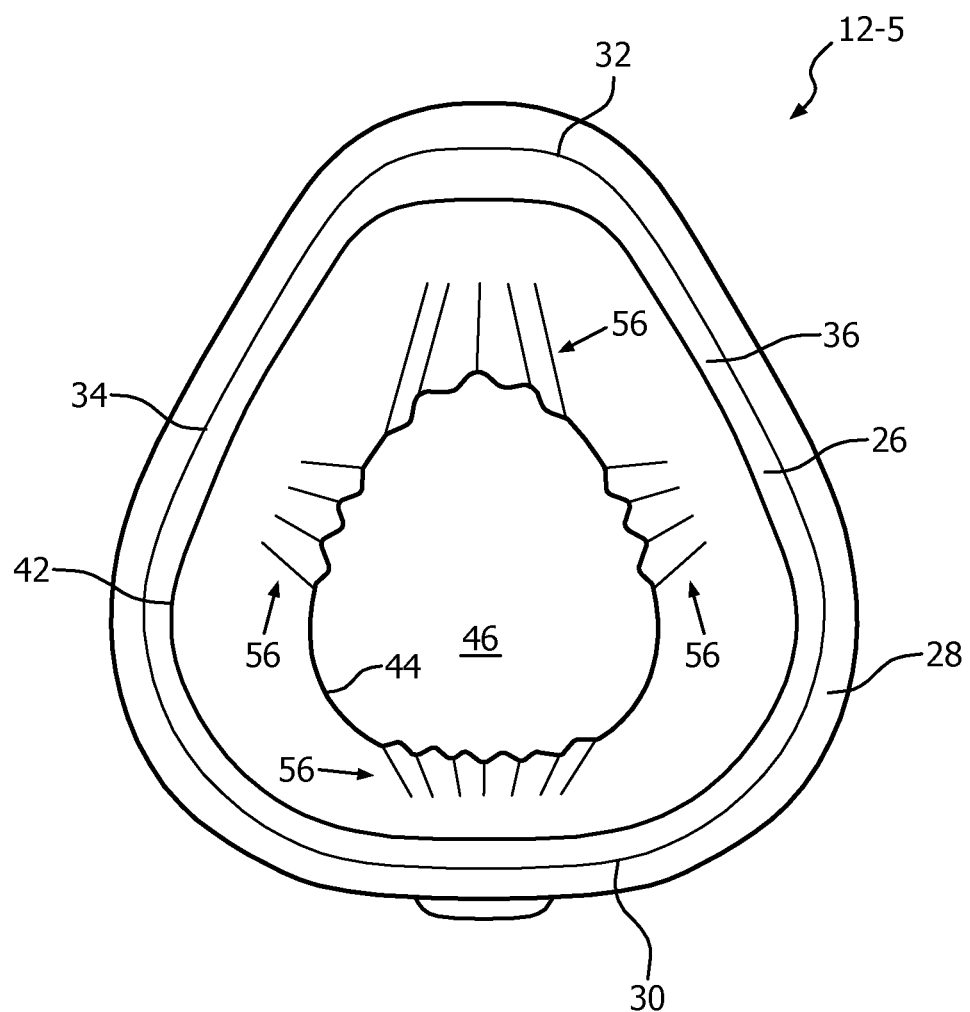

As another example, FIG. 11 is a schematic illustration of a cushion assembly 12-4 according to yet another particular, non-limiting exemplary embodiment wherein corrugated portions 56-4a and 56-4b are provided in the side regions of sealing flap 40 such that they will be engaged by the cheeks of the patient. In addition, in the non-limiting illustrated embodiment of cushion assembly 12-4, corrugated portions 56-4a and 56-4b are constructed such that furrows 58 and ridges 60 are formed in an array on an arc wherein all of the furrows 58 and all of the ridges 60 have a common focal point. FIG. 12 is a schematic illustration of a cushion assembly 12-5 according to yet another particular, non-limiting exemplary embodiment that includes corrugated portions 56 in the apex, bottom and side regions of sealing flap 40. Such corrugated portions 56 may be constructed such that furrows 58 and ridges 60 are formed in an array on an arc wherein all of the furrows 58 and all of the ridges 60 have a common focal point as described elsewhere herein.

Figure 13:
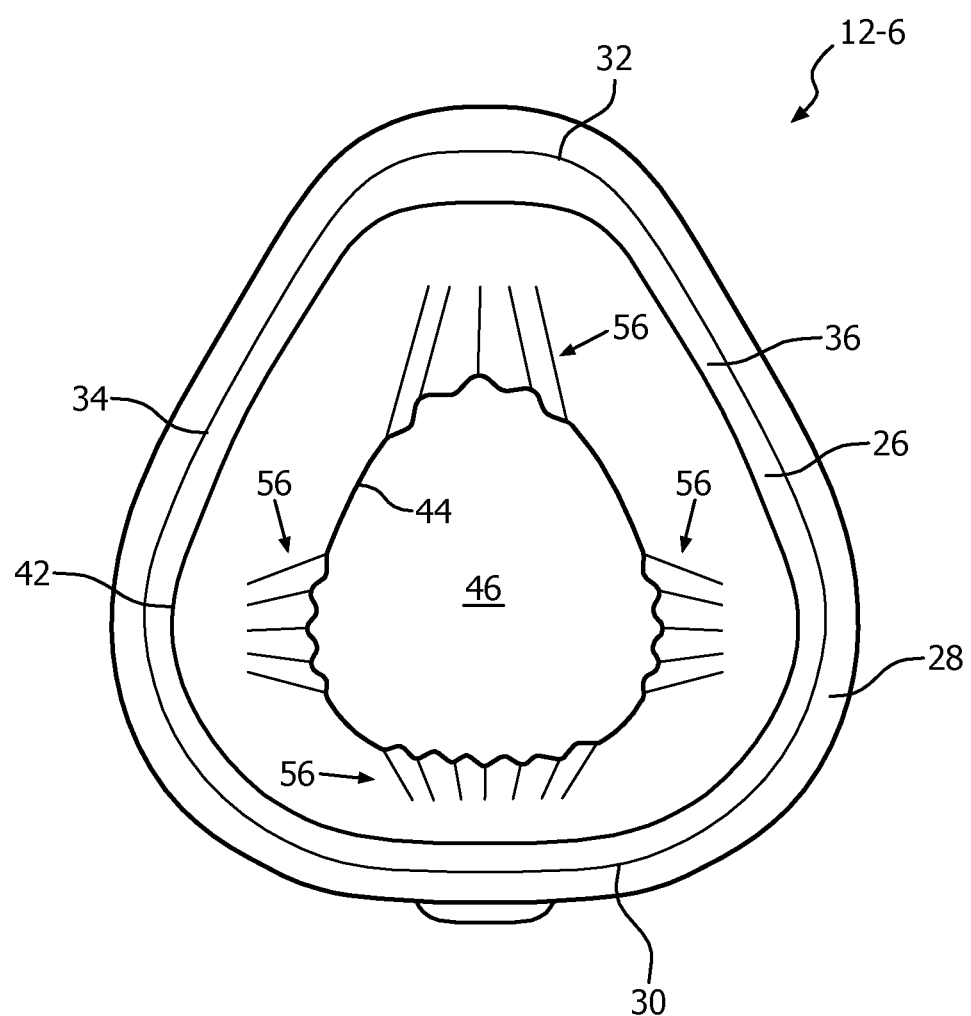

In still another alternative, in the FIG. 12 embodiment, the corrugated portions 56 in the side regions of sealing flap 40 may be omitted, leaving only the corrugated portions 56 in the apex and bottom regions of sealing flap 40. FIG. 13 is a schematic illustration of a cushion assembly 12-6 according to still another particular, non-limiting exemplary embodiment that includes corrugated portions 56 in the apex region, the bottom region, and in the portions of sealing flap 40 where the bottom region meets the side regions. Thus, in this embodiment, a corrugated portion 56 is provided at each part of the distal edge 44 of sealing flap 40 that is curved. Such corrugated portions 56 may be constructed such that furrows 58 and ridges 60 are formed in an array on an arc wherein all of the furrows 58 and all of the ridges 60 have a common focal point as described elsewhere herein.

Figure 14:
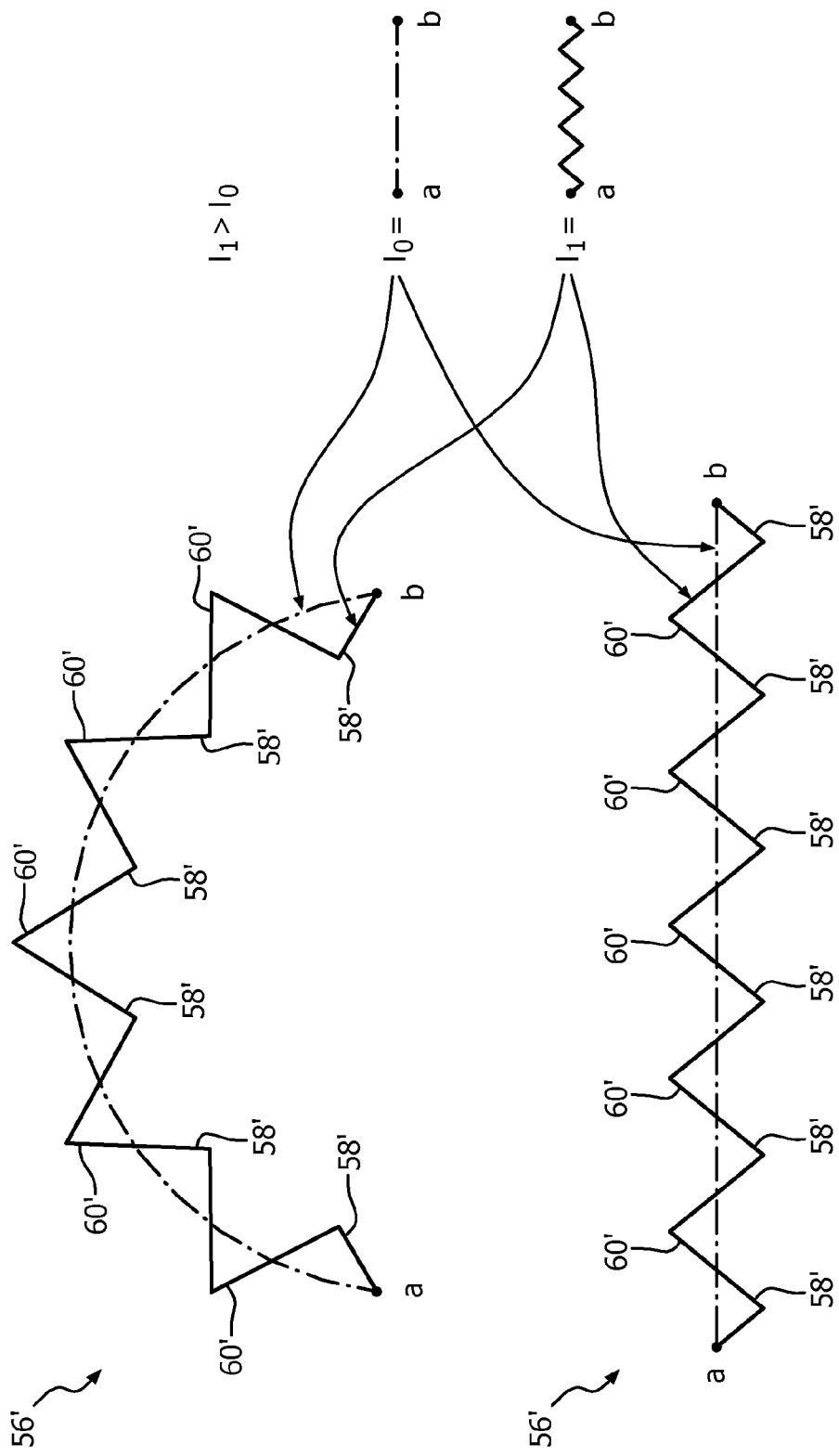
FIGS. 14-16 are schematic illustrations showing alternative corrugated portions that may be provided in a cushion assembly forming a part of a patient interface device of the system of FIG. 1.

Moreover, as seen in FIGS. 1-13, each of the corrugated portions 56 shown therein have arc-shaped (in cross-section) furrows 58 and ridges 60 such that corrugated portions 56, in cross-section, resembles a sine wave. It will be understood, however, that the embodiments of FIGS. 1-13 including the particular geometry just described is meant to be exemplary only, and that other shapes for the furrows 58 and ridges 60 shown therein are also possible. For example, FIG. 14 is a schematic illustration showing corrugated portions 56' that may be provided at curved (top of FIG. 14; e.g., apex region of sealing flap 40) or straight (bottom of FIG. 14; e.g., side regions of sealing flap 40) distal edge portions of sealing flap 40, wherein the furrows 58' and ridges 60' have a v-shaped cross-section. As a result, corrugated portions 56', in cross-section, resemble a sawtooth wave.

Figure 15:
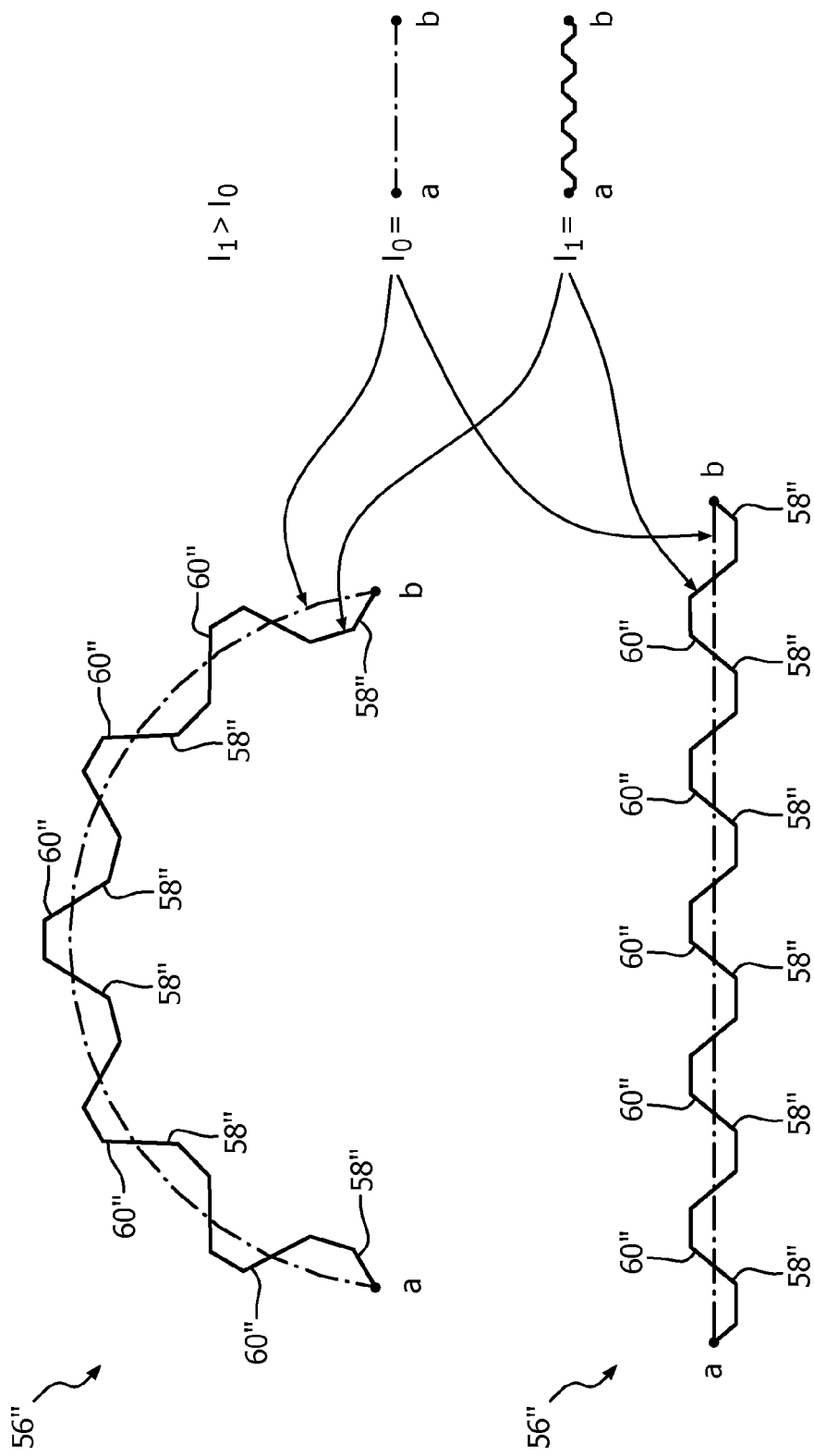
Figure 16:
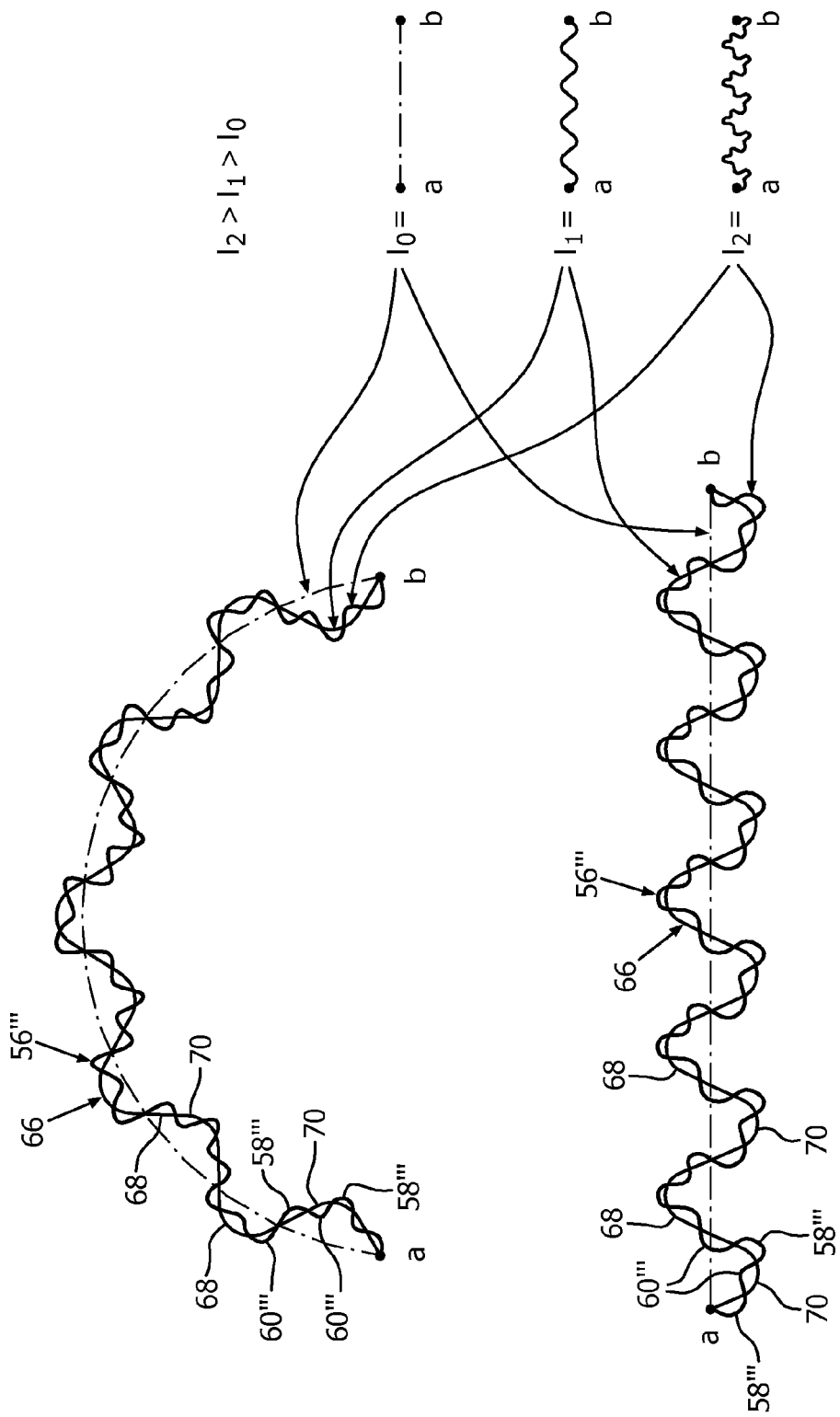

As another example, FIG. 15 is a schematic illustration showing corrugated portions 56" that may be provided at curved (top of FIG. 15; e.g., apex region of sealing flap 40) or straight (bottom of FIG. 15; e.g., side regions of sealing flap 40) distal edge portions of sealing flap 40, wherein the furrows 58" and ridges 60" have squared off bottom portions. As a result, corrugated portions 56", in cross-section, resemble an angled square wave. As still another example, FIG. 16 is a schematic illustration showing corrugated portions 56''' (superimposed for reference on a sinusoidal wave 66 similar to corrugated portions 56 having the shape shown in FIGS. 1-13 and described above), that may be provided at curved (top of FIG. 16; e.g., apex region of sealing flap 40) or straight (bottom of FIG. 16; e.g., side regions of sealing flap 40) distal edge portions of sealing flap 40. In this embodiment, corrugated portions 56''' follow a sinusoidal pattern wherein each peak 68 and valley 70 in the sinusoidal pattern includes a plurality of furrows 58''' and ridges 60'''.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for a patient interface device, comprising:
 a support wall portion having a first edge and a second edge located opposite the first edge; and
 a sealing flap extending in a cantilevered fashion inwardly from the second edge and toward a longitudinal axis of the cushion such that when the patient interface device is donned by a user a portion of the face of the user will engage a top outer surface of the sealing flap to form a seal therewith, wherein the sealing flap includes a corrugated portion, wherein the corrugated portion commences at and is provided in a terminal distal edge of the sealing flap which defines an opening in the sealing flap and extends toward a proximal edge of the sealing flap along at least a portion of a width of the sealing flap including the top outer surface, wherein the corrugated portion includes a series of alternating furrows and ridges present in the terminal distal edge, wherein each furrow and each ridge has a longitudinal axis that extends in a direction extending from the terminal distal edge to the proximal edge, and wherein a number of the furrows is at least two and a number of the ridges is at least one or a number of the ridges is at least two and a number of the furrows is at least one, wherein the corrugated portion follows a pattern having a series of peaks and valleys, and wherein each peak and each valley in the pattern includes a respective plurality of the furrows and a respective plurality of the ridges.

2. A cushion for a patient interface device, comprising:
a support wall portion having a first edge and a second edge located opposite the first edge; and
a sealing flap extending in a cantilevered fashion inwardly from the second edge and toward a longitudinal axis of the cushion such that when the patient interface device is donned by a user a portion of the face of the user will engage a top outer surface of the sealing flap to form a seal therewith, wherein the sealing flap includes a corrugated portion, wherein the corrugated portion commences at and is provided in a terminal distal edge of the sealing flap which defines an opening in the sealing flap and extends toward a proximal edge of the sealing flap along at least a portion of a width of the sealing flap including the top outer surface, wherein the corrugated portion includes a series of alternating furrows and ridges present in the terminal distal edge, wherein each furrow and each ridge has a longitudinal axis that extends in a direction extending from the terminal distal edge to the proximal edge, and wherein a number of the furrows is at least two and a number of the ridges is at least one or a number of the ridges is at least two and a number of the furrows is at least one, wherein the furrows and the ridges of the corrugated portion are formed in an array on an arc wherein all of the furrows and all of the ridges have a common focal point.

3. The cushion according to claim 2, wherein the number of the furrows is at least two and the number of the ridges is at least two.

4. The cushion according to claim 2, wherein the support wall portion and the sealing flap are part of a unitary structure.

5. The cushion according to claim 2, wherein a total amplitude to wavelength ratio within the corrugated portion for each immediately adjacent pair the furrows and the ridges is 0.4 to 0.75.

6. The cushion according to claim 5, wherein the total amplitude to wavelength ratio within the corrugated portion for each immediately adjacent pair of the furrows and the ridges is 0.5.

7. The cushion according to claim 2, wherein each of the furrows and each of the ridges is arc-shaped in cross-section.

8. The cushion according to claim 2, wherein each of the furrows and each of the ridges is v-shaped in cross-section.

9. The cushion according to claim 2, wherein the cushion has a generally triangular shape such that the sealing flap has a bottom region, an apex region located opposite the bottom region, a first side region and a second side region located opposite the first side region, wherein the corrugated portion is provided in the apex region of the sealing flap.

10. The cushion according to claim 9, wherein the sealing flap includes a second corrugated portion, wherein the second corrugated portion commences at the distal edge and extends toward the proximal edge along at least a portion of the width of the sealing flap including the top outer surface, wherein the second corrugated portion includes a series of alternating second furrows and second ridges, wherein a number of the second furrows is at least two or a number of the second ridges is at least two, and wherein the second corrugated portion is provided in the bottom region of the sealing flap.

11. The cushion according to claim 10, wherein the sealing flap includes a third corrugated portion, wherein the third corrugated portion commences at the distal edge and extends toward the proximal edge along at least a portion of the width of the sealing flap including the top outer surface, wherein the third corrugated portion includes a series of alternating third furrows and third ridges, wherein a number of the third furrows is at least two or a number of the third ridges is at least two, wherein the sealing flap includes a fourth corrugated portion, wherein the fourth corrugated portion commences at the distal edge and extends toward the proximal edge along at least a portion of the width of the sealing flap including the top outer surface, wherein the fourth corrugated portion includes a series of alternating fourth furrows and fourth ridges, wherein a number of the fourth furrows is at least two or a number of the fourth ridges is at least two.

12. The cushion according to claim 11, wherein the third corrugated portion is provided in the first side region of the sealing flap and the fourth corrugated portion is provided in the second side region of the sealing flap.

13. The cushion according to claim 11, wherein the third corrugated portion is provided in a first curved region of the sealing flap at a junction of the bottom region and the first side region of the sealing flap and the fourth corrugated portion is provided in a second curved region of the sealing flap at a junction the bottom region and the second side region of the sealing flap.

14. The cushion according to claim 9, wherein the corrugated portion is positioned in between the focal point and a portion of the opening defined by the distal edge of the sealing flap including the corrugated portion.

15. The cushion according to claim 9, wherein a portion of the opening defined by the distal edge of the sealing flap including the corrugated portion is positioned in between the focal point and the corrugated portion.

16. The cushion according to claim 2, wherein the cushion has a generally triangular shape such that the sealing flap has a bottom region, an apex region located opposite the bottom region, a first side region and a second side region located opposite the first side region, wherein the corrugated portion is provided in the bottom region of the sealing flap.

17. A patient interface device including a cushion according to claim 2.

18. A system for delivering a flow of breathing gas to a patient, comprising a pressure generating system structured to generate the flow of breathing gas and a patient interface device fluidly coupled to the pressure generating system, wherein the patient interface device includes a cushion according to claim 2.

* * * * *